(12) United States Patent
Hoffman

(10) Patent No.: US 7,545,902 B2
(45) Date of Patent: Jun. 9, 2009

(54) RECEIVED X-RAY HANDLING METHODS AND APPARATUS

(75) Inventor: David Michael Hoffman, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 214 days.

(21) Appl. No.: 11/522,597

(22) Filed: Sep. 18, 2006

(65) Prior Publication Data

US 2008/0069295 A1     Mar. 20, 2008

(51) Int. Cl.
*H05G 1/60* (2006.01)
(52) U.S. Cl. .......................... 378/5; 378/114
(58) Field of Classification Search .............. 378/19, 378/5, 114–116; 250/370.09
See application file for complete search history.

(56) References Cited

U.S. PATENT DOCUMENTS

| 4,703,424 | A | | 10/1987 | Gullberg et al. ............. 364/414 |
| 4,812,983 | A | | 3/1989 | Gullberg et al. ........ 364/413.17 |
| 5,475,727 | A | * | 12/1995 | Buchanan et al. ............. 378/53 |
| 6,264,365 | B1 | | 7/2001 | Patch ......................... 378/204 |
| 6,408,050 | B1 | * | 6/2002 | Han et al. .................. 378/98.9 |
| 7,080,063 | B2 | | 7/2006 | Campos et al. ................ 707/2 |
| 7,276,694 | B1 | * | 10/2007 | Bertsche ..................... 250/311 |

* cited by examiner

*Primary Examiner*—Hoon Song
(74) *Attorney, Agent, or Firm*—Fisher Patent Group, LLC; Thomas M. Fisher

(57) ABSTRACT

A method includes placing received x-rays into at least three bins.

17 Claims, 2 Drawing Sheets

RECEIVED X-RAY HANDLING METHODS AND APPARATUS

BACKGROUND OF THE INVENTION

This invention relates generally to diagnostic imaging methods and apparatus, and more particularly, to methods and apparatus that provide for handling of received x-rays.

Computed tomography (CT) systems sold today exclusively utilize x-ray systems that operate in a non Energy Discrimination mode as embodied by individual x-ray counting along with the measurement of each x-ray's energy. Some systems try to accomplish x-ray energy discrimination and subsequent tissue differentiation through dual KVP scanning or with layered integrating detectors.

BRIEF DESCRIPTION OF THE INVENTION

In one aspect, a method includes placing received x-rays into at least three bins.

In another aspect, a computer readable medium is embedded with a program configured to instruct a computer to bin piled up x-rays.

In still another aspect, a system is provided. The system includes an x-ray source, an x-ray detector positioned to receive x-rays emitted from the source, and a computer operationally coupled to the source and the detector, the computer is configured to place received x-rays into at least three bins.

DETAILED DESCRIPTION OF THE INVENTION

There are herein described methods and apparatus useful for imaging systems such as, for example, but not limited to an x-ray system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention.

Figure 1:
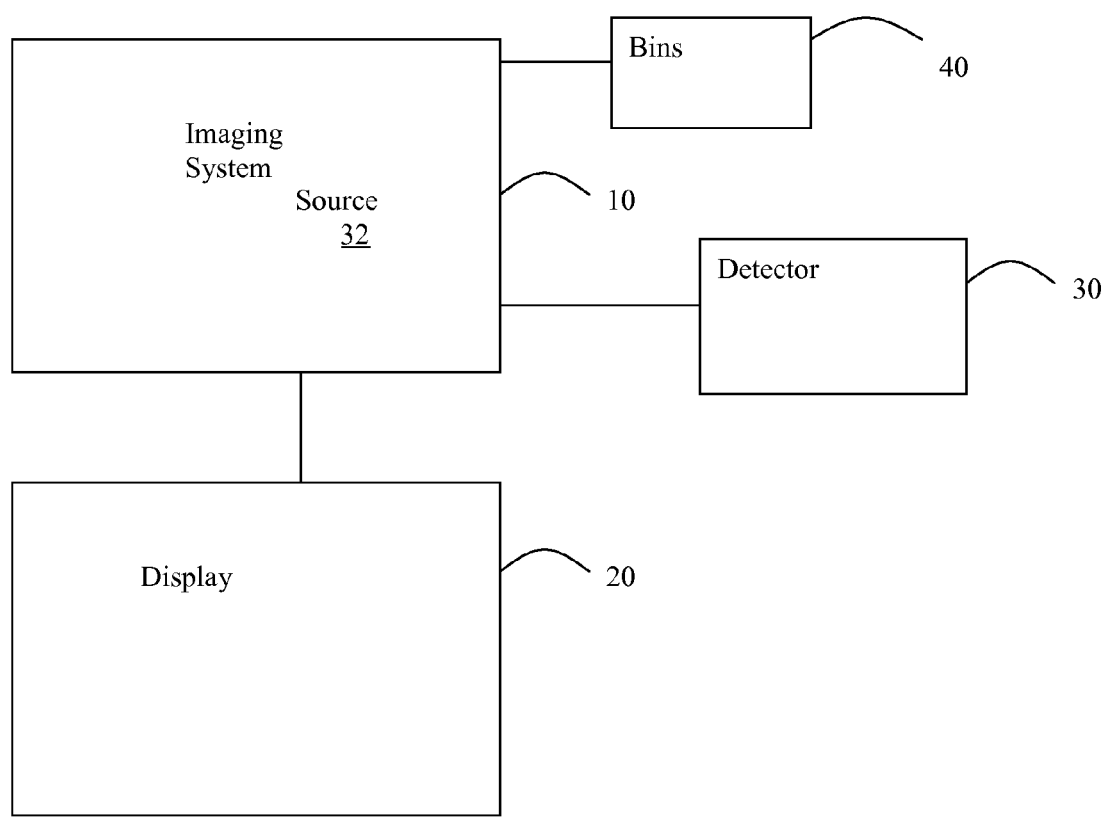
FIG. 1 illustrates an exemplary diagnostic imaging system.

FIG. 1 illustrates an imaging system 10 with an associated display 20. Imaging system 10 can be of any modality, but in one embodiment, system 10 is a CT system. In another embodiment, system 10 is a dual modality imaging system such as a combined CT/PET system and data processing can be done in one modality (e.g., CT) and the processed data can be transferred to the other modality (e.g., PET). Display 20 can be separate from system 10 or integrated with system 10. System 10 includes an acquisition device such as an x-ray radiation detector 30. X-ray detector 30 can be separate from system 10 or integrated with system 10. System 10 also includes a plurality of bins 40. Alternatively, bins 40 can be remote from system 10 if image reconstruction is not done by system 10. System 10 includes an x-ray source 32.

The x-ray imaging system includes a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. The detector may be a flat panel solid state image detector, for example, although conventional film images stored in digital form in the memory may also be processed. In one embodiment, the processing circuit executes instructions stored in firmware (not shown).

Of course, the methods described herein are not limited to practice in system 10 and can be utilized in connection with many other types and variations of imaging systems. In one embodiment, the processing circuit is a computer that is programmed to perform functions described herein, and, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research. Although the herein described methods are described in a medical setting, it is contemplated that the benefits of the invention accrue to non-medical imaging systems such as those systems typically employed in an industrial setting or a transportation setting, such as, for example, but not limited to, a baggage scanning CT system for an airport or other transportation center.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

This disclosure describes an improvement to Energy Discrimination CT systems achieved through x-ray counting along with the measurement of each x-ray's energy. It describes an improvement to systems that try to accomplish tissue differentiation through dual KVP scanning or with layered integrating detectors. The normal idea for an x-ray counting/x-ray energy detection is to have two energy bins. Every x-ray's energy is measured and then a count is added to one of two energy bins, called the low and the high energy bins. The herein described methods and apparatus provide for more energy bins which enables the measurement of information well into the pile up region of the detector, possibly up to the actual charge saturation limit of the direct conversion detector material. Although one embodiment uses a direct conversion detector material, it is contemplated the benefits the invention accrue to any detectors and the ray counting information can come from direct conversion, fast scintillators with Si-PMT's, or fast scintillators with conventional PMT's or other means.

Piled up x-rays mean x-rays that have arrived at the detector sooner than a polling trigger. In other words, assuming one polls the detector every millisecond then if x-rays arrive less than every millisecond such that two x-rays impinge a cell and when a cell is polled, the two events have merged into one, then this is a pile up. And those two x-rays are piled up. For further clarity, when the x-rays arrive more slower than one per millisecond, no pileup occurs. Put still another way, when x-rays arrive faster than the maximum resolvable detector count rate, then pile up occurs. And when x-rays arrive slower than the maximum resolvable detector count rate, then pile up does not occur.

The extra energy bins could be any number of bins and with any number of possible energy values or ranges. One such energy bin energy scenario could be a low energy bin, a high energy bin, a low+high energy bin, a 2× high energy bin, etc., thus extending the number of energy bins from maybe two to say for example eight bins. The herein described methods and apparatus would allow piled up x-rays to be measured at an artificially aggregated higher energy and binned accordingly. As the pile up curve increased the usefulness of the counting information would decrease, but then instead of the accurate counting information, one would use an integration of the energy, or the summation of the number of counts in every bin times the average energy of the bin. These counts would be piled up but would still be representative of accurate energy information, up to the saturation limit of the detector. The herein described methods and apparatus would enable the x-ray counting detectors to act in a count mode for a certain dynamic range, followed by an energy integrating mode through out a wider dynamic range, up to possibly the saturation limit of the detector.

Figure 2:
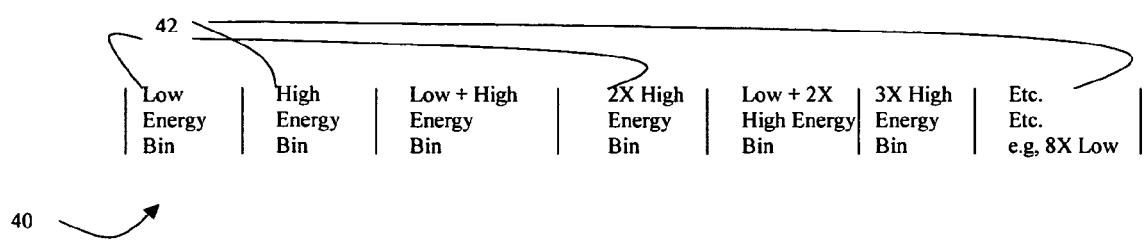
FIG. 2 illustrates bins.

FIG. 2 illustrates bins 40 including a plurality of individual bins 42. The bins 42 may or may not be integral multiples of each other. In one embodiment, the bins include a first bin from about zero to about 60 keV, a second bin from about 60 keV to about 120 keV, a third bin from about 120 keV to 180 keV and a fourth bin from about 180 keV and above. In other embodiments, other ranges are used. For example the first range can be from zero to 70 or zero to 80 keV. The second bin can be from 50 to 130 or from 70 to 110. the third bin can be from 110 to 190. Or, from 130 to 170. And similarly with the fourth bin.

Technical effects include that the herein described methods and apparatus is that having many more energy bins enables the measurement of information well into the pile up region of the detector, possibly up to the actual charge saturation limit of the direct conversion detector material. The herein described methods and apparatus could be a key enabler for a premium type x-ray counting CT system. The herein described methods and apparatus would allow piled up x-rays to be measured at an artificially aggregated higher energy and binned accordingly. The herein described methods and apparatus would enable the x-ray counting detectors to act in a count mode for a certain dynamic range, followed by an energy integrating mode through out a wider dynamic range, up to possibly the saturation limit of the detector. The herein described methods and apparatus could enable x-ray counting and energy measurement CT detectors with all the associated application and patient benefits.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method comprising:
receiving at least one x-ray at a radiation detector;
repeatedly polling the radiation detector obtaining a plurality of energy measurement counts; and
binning the counts into at least three bins such that piling up of x-rays is accounted for, wherein the bins each have a respective average energy and a respective number of counts, said method comprising summing the number of counts in each bin times the average energy of that bin and storing that sum in a memory.

2. A method in accordance with claim 1 wherein said binning the counts comprises binning the counts into at least four bins.

3. A method in accordance with claim 1 wherein said bins are integral multiples of each other.

4. A method in accordance with claim 1 wherein said bins comprise a first bin from about zero to about 60 keV, a second bin from about 60 keV to about 120 keV, and a third bin from about 120 keV and above.

5. method in accordance with claim 2 wherein said bins comprise a first bin from about zero to about 60 keV, a second bin from about 60 keV to about 120 keV, a third bin from about 120 keV to 180 keV and a fourth bin from about 180 keV and above.

6. A computer readable medium embedded with a program configured to instruct a computer to:
bin piled up x-rays by measuring an energy level of the x-rays to count x-rays of different energies and/or multiple x-rays of approximately the same energy; and
binning the counts into at least three bins such that piling up of x-rays is accounted for, wherein the bins each have a respective average energy and a respective number of counts, said program further configured to instruct the computer to sum the number of counts in each bin times the average energy of that bin and store that sum in memory.

7. A computer readable medium in accordance with claim 6 wherein the x-rays were detected with a direct conversion medium.

8. A computer readable medium in accordance with claim 6 wherein said program further configured to instruct the computer to bin counts of x-rays such that there is at least three bins.

9. A computer readable medium in accordance with claim 6 wherein said program further configured to instruct the computer to bin counts of x-rays such that there is at least four bins.

10. A computer readable medium in accordance with claim 6 wherein the bins comprise a first bin from about zero to about 60 keV, a second bin from about 60 keV to about 120 keV, and a third bin from about 120 keV and above.

11. A computer readable medium in accordance with claim 6 wherein the bins comprise a first bin from about zero to about 60 keV, a second bin from about 60 keV to about 120 keV, a third bin from about 120 keV to 180 keV and a fourth bin from about 180keV and above.

12. A system comprising:
an x-ray source;
an x-ray detector positioned to receive x-rays emitted from said source; and
a computer operationally coupled to said source and said detector, said computer configured to measure energies of a plurality of received x-rays creating counts and placing those counts into at least three bins, wherein the bins each have a respective average energy and a respective number of counts, said computer further configured to sum the number of counts in each bin times the average energy of that bin.

13. A system in accordance with claim 12 wherein said computer further configured to place counts into at least four bins.

14. A system in accordance with claim 12 wherein the bins are integral multiples.

15. A system in accordance with claim 12 wherein the bins comprise a first bin from about zero to about 60 keV, a second bin from about 60 keV to about 120 keV, and a third bin from about 120 keV and above.

16. A system in accordance with claim 12 wherein the bins comprise a first bin from about zero to about 60 keV, a second bin from about 60 keV to about 120 keV, a third bin from about 120 keV to 180 keV and a fourth bin from about 180 keV and above.

17. A system in accordance with claim 12 wherein the x-rays were detected with a direct conversion medium.

* * * * *